United States Patent
Imperante et al.

(10) Patent No.: US 6,586,465 B1
(45) Date of Patent: Jul. 1, 2003

(54) ESTERS

(76) Inventors: John Imperante, 60 Fourth St., Somerville, NJ (US) 08876; Anthony J. O'Lenick, Jr., 2170 Luke Edwards Rd., Dacula, GA (US) 30019

( * ) Notice: Subject to any disclaimer, the term of this patent is extended or adjusted under 35 U.S.C. 154(b) by 0 days.

(21) Appl. No.: 10/157,529

(22) Filed: May 30, 2002

(51) Int. Cl.⁷ ................... A61K 31/357; C07D 317/14; C07D 319/06
(52) U.S. Cl. ................ 514/452; 514/467; 549/372; 549/453
(58) Field of Search ................. 514/452, 467; 549/372, 453

(56) References Cited

U.S. PATENT DOCUMENTS 5,488,121 A    1/1996    O'Lenick

*Primary Examiner*—Taofiq Solola

(57) ABSTRACT

The present invention deals with the certain novel esters derived from specific cyclic ether containing alcohols. These products have surprising hydroalcoholic solubility and a very desirable skin feel, making them ideal candidates for use in products like after shave preparations.

19 Claims, No Drawings

ESTERS

BACKGROUND OF THE INVENTION

1. Field of the Invention

The present invention deals with the certain novel esters derived from specific cyclic ether containing alcohols. These products have surprising hydroalcoholic solubility and a very desirable skin feel, making them ideal candidates for use in products like after shave preparations.

2. Description of the Art Practices

Fatty alcohols have been known for many years, primarily for their liquidity at high molecular weight. Over the years there have been a number of derivatives patented.

U.S. Pat. No. 4,868,236 to O'Lenick discloses a Guerbet citric ester and polymers thereof useful in plastic lubrication.

U.S. Pat. No. 5,488,121 issued Jan. 30, 1996 to O'Lenick teaches that esters based upon a Guerbet acid and Guerbet alcohols have surprisingly good liquidity.

None of these materials offer the hydroalcoholic solubility and unique dry skin feel as do the compounds of the present invention. Both of these desirable properties are a direct consequence of the proper selection of the cyclic ether containing alcohol and the proper fatty acid used to make the ester.

THE INVENTION

3. Objective of the Invention

It is the objective of the present invention to provide novel ester compositions, based upon (a) fatty acids and (b) an ether containing alcohol, which when both present in the same molecule result in an ester that exhibits outstanding hydroalcoholic solubility and excellent skin feel, heretofore unattainable.

It is another objective of the present invention to provide a process for conditioning skin by applying an effective conditioning concentration of the novel ester compositions, based upon (a) fatty acids and (b) a novel ether containing alcohol.

Other objectives will become apparent reading the present teachings.

SUMMARY OF THE INVENTION

The compositions of the present invention are mixtures of compounds conforming to the following structures:

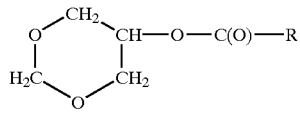

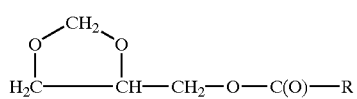

wherein;

R is

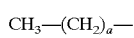

wherein a is an interger ranging from 6 to 20.

DETAILED DESCRIPTION OF THE INVENTION

The compositions of the present invention are made by the esterification of a mixture of two novel ether alcohols conforming to the following structures:

(a) a six member ringed ether alcohol

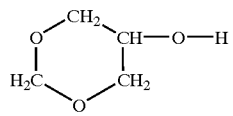

and (b) a five member ringed ether alcohol

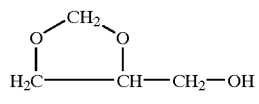

The mixture is commercially available and the ratio of (a) to (b) ranges from 0.8:1 to 1.0 to 0.8, with a ratio of 1:1 being most desired.

with a fatty acid conforming to the following structure;

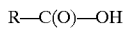

R is

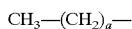

wherein a is an interger ranging from 6 to 20.

Another aspect of the present invention is a process for conditioning skin, which comprises contacting the skin with an effective conditioning concentration of a composition conforming to the following formula;

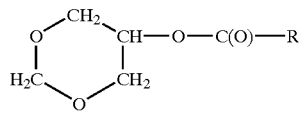

and

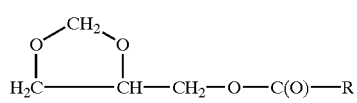

wherein;

R is

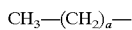

wherein a is an interger ranging from 6 to 20.

PREFERRED EMBODIMENTS

In a preferred embodiment the concentration of

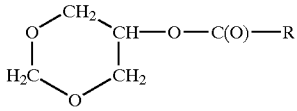

is 100% by weight

In another preferred embodiment the concentration of

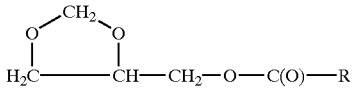

is 100% by weight.

In a preferred embodiment a is 6.
In a preferred embodiment a is 10.
In a preferred embodiment a is 12.
In a preferred embodiment a is 14.
In a preferred embodiment a is 16.
In a preferred embodiment a is 18.
In a preferred embodiment a is 20.
In a preferred embodiment a is an integer ranging from 6 to 20.
In a preferred embodiment a is an integer ranging from 10 to 16.
In a preferred embodiment, the effective conditioning concentration ranges from 0.1 to 20% by weight.
In a preferred embodiment, the effective conditioning concentration ranges from 1 to 10% by weight.

EXAMPLES

Raw Materials

Ether Amine Alcohols

The ether cyclic alcohols are commercially available from Phoenix Chemical Somerville, N.J. either as pure materials or as a blend having a 50/50 composition.

(a) six member ringed ether alcohol

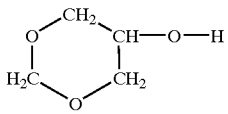

(b) five member ringed ether alcohol

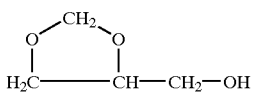

Alcohols
Alcohol Composition (% by weight)

| Example | Five member ring ether alcohol | Six member ring ether alcohol |
|---|---|---|
| 1 | 100 (% by wt) | 0 (% by wt) |
| 2 | 0 (% by wt) | 100 (% by wt) |
| 3 | 60 (% by wt) | 40 (% by wt) |
| 4 | 40 (% by wt) | 80 (% by wt) |

Fatty Acids

Fatty Acids are commercially available from a variety of sources including Cognis Chemical (Cincinnati Ohio).

| Example | Common Name | a |
|---|---|---|
| 5 | Octanoic Acid | 6 |
| 6 | Decanoic Acid | 8 |
| 7 | Lauric Acid | 10 |
| 8 | Palmitic Acid | 12 |
| 9 | Stearic Acid | 16 |
| 10 | Behenic Acid | 20 |

Ester Synthesis

The esterification reaction is carried out using an excess of ether alcohol or acid or more typically using an equivalent of each. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

General Procedure

To the 104.0 grams of the specified ether alcohol (Example 1–4) is added the specified number of grams of the specified fatty acid (Examples 5–10). Next add 0.1 % stannous oxylate the total weight of the batch after all ingredients have been charged, under agitation. The temperature of the mass is raised to 180–200° C. and water is stripped off as formed. The acid value and hydroxyl value drop to vanishingly small values.

|  | Fatty Acid | | Ether Alcohol |
|---|---|---|---|
| Example | Example | Grams | Example |
| 7 | 1 | 144.0 | 1 |
| 8 | 2 | 172.0 | 2 |
| 9 | 3 | 200.0 | 3 |
| 10 | 4 | 228.0 | 4 |
| 11 | 5 | 284.0 | 1 |
| 12 | 6 | 340.0 | 2 |

APPLICATIONS EXAMPLES

Hydroalcoholic solubility is defined as the ability of an ester to be soluble in a mixture of ethanol and water. The compounds of the present invention, because of the specific cyclic ether alcohol used in their preparation are soluble in mixtures of ethanol and water. They also have a very cosmetically acceptable feel on the skin and consequently are useful in the preparation of after shave and pre-shave products.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. A composition comprising the following formula;

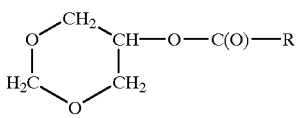

and

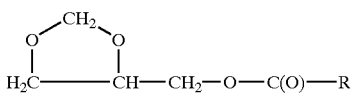

wherein;

R is

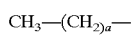

wherein
a is an interger ranging from 6 to 20.

2. A composition of claim 1 wherein the concentration of

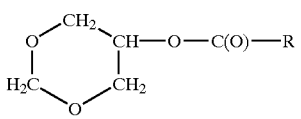

is 100% by weight.

3. A composition of claim 1 wherein the concentration of

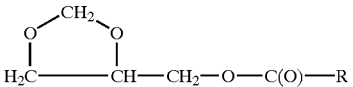

is 100% by weight.

4. A composition of claim 1 wherein a is 6.
5. A composition of claim 1 wherein a is 8.
6. A composition of claim 1 wherein a is 10.
7. A composition of claim 1 wherein a is 12.
8. A composition of claim 1 wherein a is 14.
9. A composition of claim 1 wherein a is 16.
10. A composition of claim 1 wherein a 18.
11. A composition of claim 1 wherein a is 20.
12. A composition of claim 2 wherein a is an integer ranging from 6 to 20.
13. A composition of claim 3 wherein a is an integer ranging from 6 to 20.
14. A composition of claim 2 wherein a is an integer ranging from 10 to 16.
15. A composition of claim 3 wherein a is an integer ranging from 10 to 16.
16. A composition of claim 2 wherein a is an integer ranging from 12 to 14.
17. A composition of claim 3 wherein a is an integer ranging from 12 to 14.
18. A composition of claim 2 wherein a is 12.
19. A composition of claim 3 wherein a is 12.

* * * * *